United States Patent
Gallardo Inzunza

(10) Patent No.: US 9,693,900 B2
(45) Date of Patent: Jul. 4, 2017

(54) INTRAOCULAR PRESSURE COMPENSATING AND REGULATING VALVE

(71) Applicant: Manuel Humberto Gallardo Inzunza, Cullacan (MX)

(72) Inventor: Manuel Humberto Gallardo Inzunza, Cullacan (MX)

(*) Notice: Subject to any disclaimer, the term of this patent is extended or adjusted under 35 U.S.C. 154(b) by 405 days.

(21) Appl. No.: 14/056,018

(22) Filed: Oct. 17, 2013

(65) Prior Publication Data

US 2015/0045716 A1    Feb. 12, 2015

(30) Foreign Application Priority Data

Aug. 6, 2013   (MX) .................... MX/a/2013/009123

(51) Int. Cl.
*A61F 9/007*    (2006.01)

(52) U.S. Cl.
CPC .............................. *A61F 9/00781* (2013.01)

(58) Field of Classification Search
CPC .................................................. A61F 9/00781
See application file for complete search history.

(56) References Cited

U.S. PATENT DOCUMENTS

| 3,788,327 | A | 1/1974 | Donowitz et al. |
| 6,203,513 | B1* | 3/2001 | Yaron ................. A61F 9/00781 604/264 |
| 2011/0105986 | A1* | 5/2011 | Bronstein ........... A61F 9/00781 604/8 |

* cited by examiner

*Primary Examiner* — Leslie Deak
*Assistant Examiner* — Kai Weng
(74) *Attorney, Agent, or Firm* — Cook Alex Ltd.

(57) ABSTRACT

An intraocular pressure compensating and regulating valve installed inside the eye's cornea includes: a valve body having a valve seat at an end; a mobile element connected to the valve seat under normal intraocular pressure conditions inside the eye, the mobile element being configured such that it can be separated from the valve seat when the intraocular pressure exceeds the intraocular pressure limit; and an element to keep the mobile element in contact with the valve seat.

10 Claims, 5 Drawing Sheets

INTRAOCULAR PRESSURE COMPENSATING AND REGULATING VALVE

FIELD OF THE DISCLOSURE

The present disclosure refers to devices to use in glaucoma treatment, and specifically to a device to reduce intraocular pressure.

BACKGROUND OF THE DISCLOSURE

Glaucoma is an ocular disorder characterized in that it is a neuropathy in which several mechanisms causing damage and loss of retinal ganglion cells intervene, one of the main factors and to date a controllable factor is that of intraocular pressure, and an objective of the disclosure is to keep the intraocular pressure at a normal level. One of the theories is that cell damage is caused by the elevated intraocular pressure that by means of mechanical action causes compression of the nervous fibers and consequently damage to the optical nerve, which is expected to gradually lead to irreversible damage to ganglion cells, nervous fibers and atrophy of the optical nerve and consequently damage and visual field loss until eyesight is lost completely.

The frontal part of the eye is filled with a clear liquid called aqueous humor, which is primarily produced in the ciliary passages found behind the iris. This liquid exits or is removed from the eye through canals in the frontal part thereof, in an area called the anterior chamber angle, at times simply referred to as "angle."

A normal eye has been generally considered as having a normally appropriate intraocular pressure of about 10 to about 20 mm Hg, through the circulation inside the aqueous humor of the eye, which is secreted from the ciliary body, goes through the pupil to the anterior chamber of the eyeball, and is filtered outside the eyeball through the trabecular meshwork and the Schlemm's canal. When the aqueous humor excreting passageway is blocked, the aqueous humor cannot leave the eyeball at a suitable speed, the intraocular pressure is increased, the eyeball hardens, and direct damage is produced, subsequently developing atrophy of the optical nerve, which is called glaucoma. A characteristic optical neuropathy is developed, resulting in progressive loss of ganglion cells of the retina, visual field restriction, and finally producing blindness. The advanced stages of the illness are also characterized by significant pain.

Treatment for glaucoma, if started early in the course of the illness, may avoid additional damage and preserve the most of the ocular functions. The object of glaucoma treatment is to reduce the intraocular pressure until reaching a level considered safe particularly for the sight, but which is not so low as to cause an ocular malfunction or retinal complications.

There are diverse and varied techniques for treating intraocular high pressure "deviating" the aqueous humor to adjacent tissues contained inside the eyeball, all beneath the sclera or conjunctiva, this technique being subject to the ability of absorbing each one of the tissues wherein the liquid causing the elevated intraocular pressure is canalized.

Typical ophthalmic implants have a valve mechanism to regulate the aqueous humor flow from the anterior chamber; defects in and/or failure of said valve mechanisms can lead to an excessive loss of aqueous humor from the eyeball and possible hypotony. The implants also tend to be obstructed as time goes by, whether from the interior by the tissue, such as the iris, being inhaled at the entrance, or from the exterior by cell proliferation, for example, by forming scars. Furthermore, typical operation of inserting the implant is complicated, highly traumatic and takes a long time.

U.S. Pat. No. 3,788,327 shows an implant from the state of the art using a valve mechanism for regulating the aqueous humor flow from the eyeball to its exterior.

The deficiency and main drawback of this device is the existence of a gap or cavity between the upper part of its liquid-releasing mechanism and the output hole located in the exterior of the eye that is directly connected to the environment and eyelids; since said cavity is highly inclined to organic and inorganic matter sedimentation that will restrict or impede free movement of the release mechanism and/or will generate an obstruction (clogging) in the aqueous humor exit channel, thus resulting in deficiency of its performance and draining capacity of aqueous humor and increasing the intraocular pressure.

The functioning of this device and draining capacity is unsafe since it is conditioned to free movement in its release mechanism, free fluid conduction and the lack of obstacles in the channel removing the aqueous humor towards the outside of the eye and does not have any mechanism nor measures to impede forming these restrictions and/or obstructions.

Another drawback or deficiency of this device results in its high feasibility of establishing bacterial colonies in the cavity existing between the upper part of its liquid release mechanism and the output hole located outside the eye, since this channel does not have any mechanism or measure to impede the formation and accumulation of bacteria as well as the eye's own secretions.

This device has a high endophtalmitis risk, since clogging the channel existing in the upper part of the release mechanism will cause an aqueous humor blockage in its inside, and thus bacteria will find here a favorable niche for its rapid development and entrance to the inside of the eye.

As previously mentioned, the defects and/or failure in the mechanism and drainage of the valve could lead to increasing the intraocular pressure.

The device of the present disclosure does not depend on the capacity of absorption of any tissue to remove the aqueous humor without obstructions between its spindle and the outside. Also, its implant process is the least traumatic possible, typically requiring only ambulatory or out-patient surgery, the device or valve of the disclosure being based on its design simplicity and components. The present valve comprises an interior part or chassis and a stem that is displaced outside in the corneal surface (over the epithelium), the valve stem is subject to a tension caused by a compression spring or the repulsion between two permanent magnets, this spring or the magnetic repulsion are calibrated to a given tension (about 10 to about 20 mm Hg), and when the eyeball reaches the tension value greater than the spring or the repulsion, it achieves displacement of the stem outside the cornea, such that the aqueous humor causing the elevated intraocular pressure can be drained outside the eye. Once the pressure is regulated, the stem returns to its initial position tightly closing the valve and thus avoiding any entrance of foreign objects, such as dust, microorganisms, etc., into the eye.

There are very clear and precise advantages between the device of the present disclosure and the devices from the state of the art. These include:

Regulating pressure is always constant, and the aqueous humor flow is free of obstacles.

The smooth exterior upper surface of the device allows cleaning and constant lubrication through the natural movement of the eyelids impeding formation of sediments and bacteria build-up.

The lack of interior and exterior cavities impedes the formation of sediments and bacteria build-up.

The drainage mechanism is always free and lacks movement restrictions; thus its functioning does not have conditions.

This type of configuration allows a laminar flow of the aqueous humor through the device walls to achieve a sweeping effect and thus avoid adherence of bacterial strains.

The present disclosure provides an intraocular pressure compensating and regulating valve installed on the cornea of an eye, comprising: a valve body having a valve seat on one end; a mobile element in contact with the valve seat under normal intraocular pressure conditions in the eye; the mobile element is configured such that it can be separated from the valve seat when the intraocular pressure exceeds an intraocular pressure limit; and an element is provided to keep the mobile element in contact with the valve seat. The valve body has an exterior part with fastening elements to retain the valve to the cornea, and the intraocular pressure limit is from about 10 to about 20 mm Hg.

In a first embodiment, the element to keep the mobile element in contact with the valve seat is a spring placed on an interior part of the valve body, and the mobile element is a stem comprising a tubular body with an internal canal therein, the stem having on its upper part perforations for allowing the aqueous humor exit the valve.

In a second embodiment, the element to keep the mobile element in contact with the valve seat is constituted by two permanent magnets with the same polarity placed on an interior part of the valve part, and the mobile element is a stem comprising a tubular body with an internal canal therein, the stem having on its upper part perforations for allowing the aqueous humor exit the valve.

In a third embodiment, the mobile element is a stem comprising a tubular body with an internal canal therein, and the element for keeping the mobile element in contact with the valve seat is constituted by two springs placed in contact with one valve body end opposite the end where the valve seat is and a ring located in the stem, the stem having on its upper part perforations for allowing the aqueous humor exit the valve.

In a fourth embodiment, the element to keep the mobile element in contact with the valve seat is a spring having a first end and a second end, the spring is located in an interior part of the valve body, and the mobile element is a pad having on its lower part a hoop to fasten a first end of the spring; and the second end of the spring is attached to a fastening element located on the inside part of the valve body.

BRIEF DESCRIPTION OF THE DRAWINGS

For a better understanding of the present disclosure, a description thereof is provided below, along the attached drawings, wherein.

DETAILED DESCRIPTION

Figure 1:
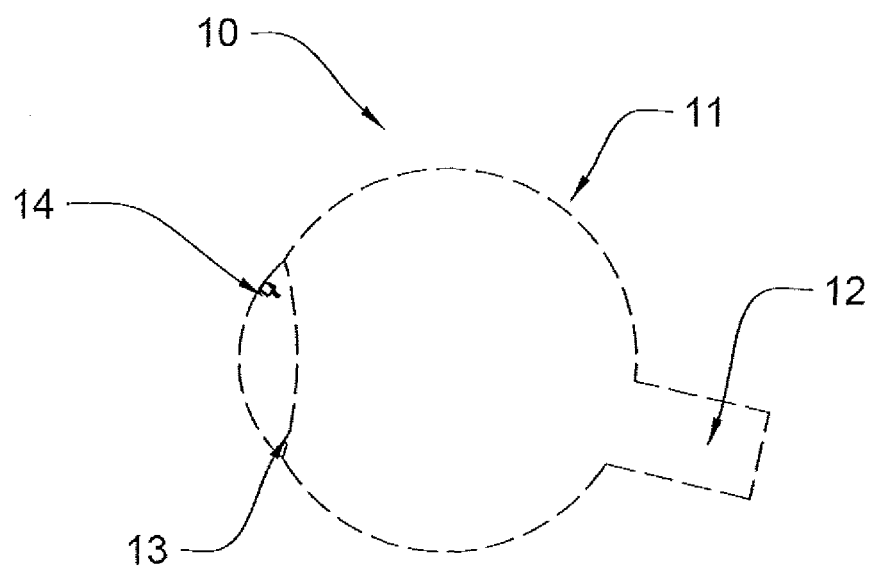
FIG. 1 is a sectional somewhat schematic view of an eye showing the location of a valve of the present disclosure.

With reference to FIG. 1, an eye 10 is shown indicating the eyeball 11, the optical nerve 12 and the cornea 13 in which the intraocular pressure compensating and regulating valve 14 is implanted. Said valve 14 allows release of aqueous humor outside the eye, when the threshold pressure is exceeded to which the valve 14 is calibrated.

Figure 2:
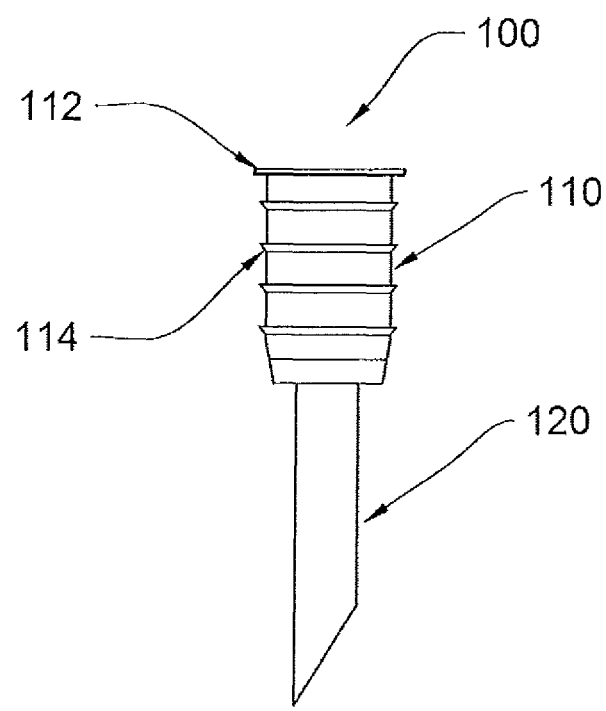
FIG. 2 is a side elevational view of the valve of the disclosure in a first embodiment.
Figure 3:
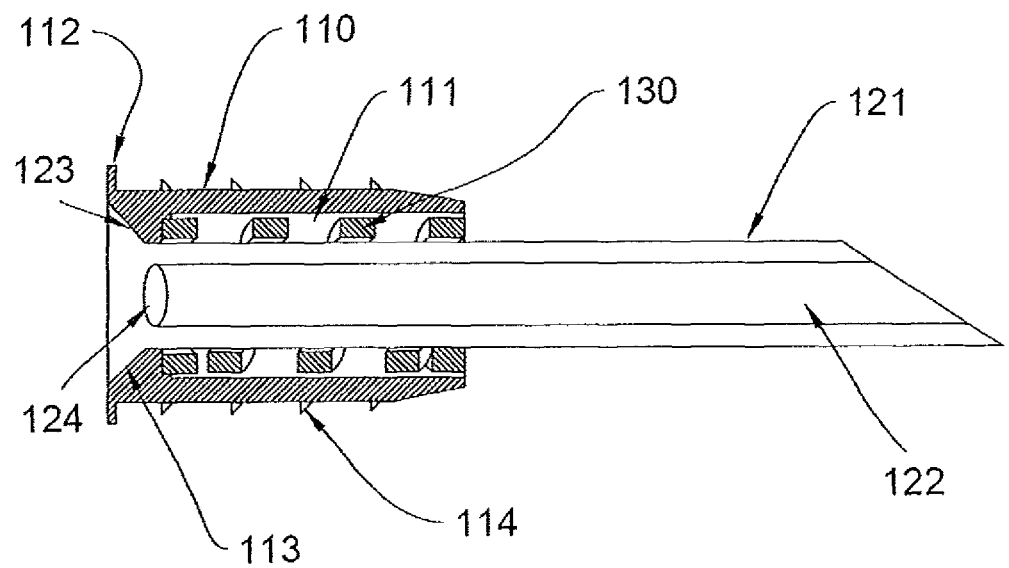
FIG. 3 is a longitudinal sectional view of the first embodiment of the valve of FIG. 2.

A first embodiment of the intraocular pressure compensating and regulating valve 100 is illustrated in FIGS. 2 and 3, and comprises a valve body or sheath 110, a stem 120 and a spring 130. The valve body 110 has a hollow tubular body 111 and a flange 112 in a tubular body 111 end. The stem 120 comprises a tubular body 121 with an internal canal 122 having in one of its ends, a conical part 123 resting on a seat 113, which is also conical at the location where the flange 112 is located in the valve body 110. The tubular body 121 of the stem 120, beneath the conical part 123, has radial perforations 124 in communication with the internal canal 122 of the tubular body 111 of the stem 120.

The valve body 110 includes the spring 130 in the internal part of the hollow tubular body 111, to keep the stem 120 pressured such that the conical part 123 is seated on seat 113 of the valve body 110. The hollow tubular body 111 includes fastening elements 114 to retain and fasten the valve 100 to the cornea. The spring 130 is tightened to the stem 120 and the other one of the ends of the spring is not tightened to the stem but there is a separation with the stem 120 from about 5 to about 10 microns, such that the stem 120 can be displaced outside the valve body 110.

Under normal conditions of intraocular pressure (10-20 mm Hg), valve 100 remains closed and there is no aqueous humor flow outside. However, when the intraocular pressure exceeds the limit to which the spring 130 is calibrated, the stem 120 is displaced defeating the spring's 130 strength and thus the conical part 123 of the stem 120 is separated from the seat 113 of the valve body 110 allowing the aqueous humor to flow through the internal canal 122 and the radial perforations 124 of the stem 120 expelling the aqueous humor. Once the pressure is regulated, stem 120 returns to its initial position tightly closing valve 100 and thus avoiding any entrance of foreign objects to the eye (dust, microorganisms, etc.).

Figure 4:
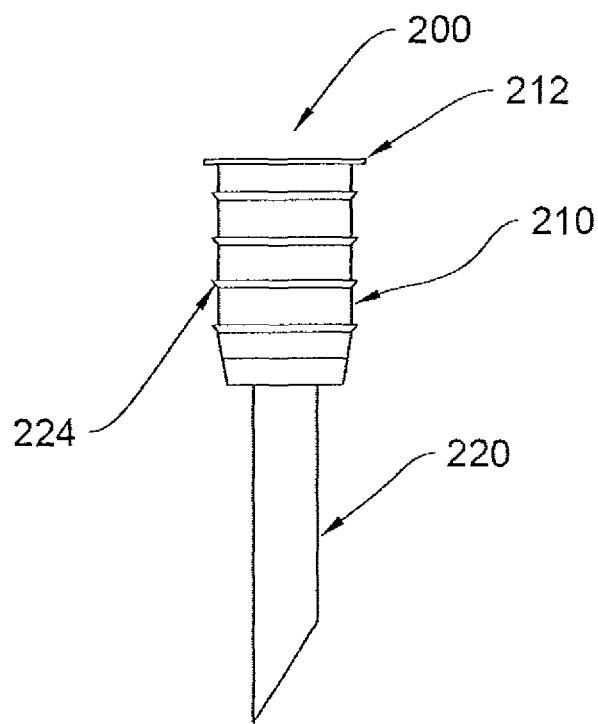
FIG. 4 is a side elevational view of a valve of the disclosure in a second embodiment.
Figure 5:
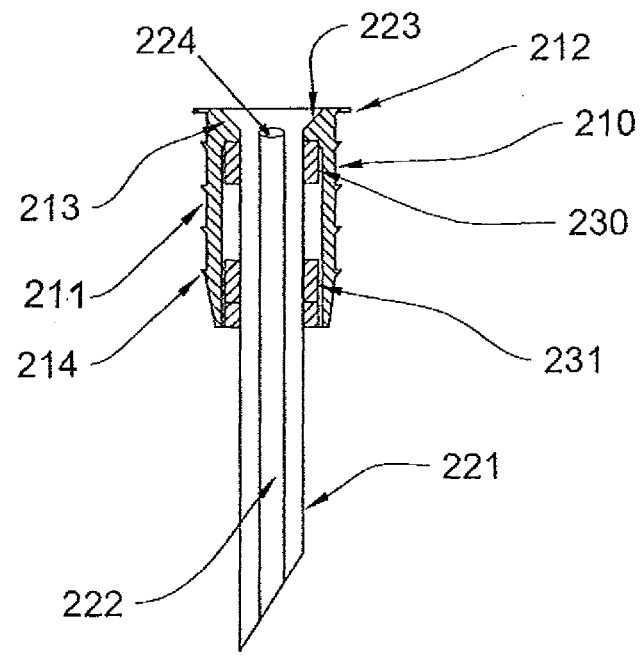
FIG. 5 is a longitudinal sectional view of the second embodiment of the valve of FIG. 4.

In a second embodiment, such as is illustrated in FIGS. 4 and 5, the intraocular pressure compensating and regulating valve 200 comprises one valve body 210 or sheath, a stem 220 and two circular magnets (230 and 231). The valve body 210 has a hollow tubular body 211 and a flange 212 at a tubular body 211 end. The stem 220 comprises a tubular body 221 with an internal canal 222 having on one of its ends, a conical part 223 resting upon a seat 213, which is also conical in the part wherein the flange 212 is located in the valve body 210. The stem 220 tubular body, beneath the conical part 223, has radial perforations 224 in communication with the internal canal 222 of the tubular body 221 of the stem 220.

The valve body 210 includes the first circular permanent magnet 230 placed on the internal part of the hollow tubular body 211 at the end where the flange 212 of the valve body 210 is located. The second circular permanent magnet 231 is placed on stem 220 at the other end level of the valve body 210, such that magnets (230 and 231) are separated by a distance. The polarity of the first magnet is equal to that of the second magnet in order to obtain a repulsion strength between the magnets, and thus to keep the conical part 223 resting on seat 213 of the valve body 210. The hollow tubular body 211 includes fastening elements 214 to retain and attach the valve 200 to the cornea. The second magnet 231 is tightened to stem 220 and the first magnet 230 is not tightened to the stem but there is a separation with the stem 220 from about 5 to about 10 microns, such that stem 220 can be displaced outside the valve body 210.

When the intraocular pressure exceeds the limit to which the repulsion strength is calibrated (e.g., about 10 to about 20 mm Kg), the stem 220 is displaced defeating the repulsion strength and thus the conical part 223 of stem 220 is separated from the seat 213 of the valve body 210 allowing the aqueous humor to flow through the internal canal 222 at the radial perforations 224 of stem 220 expelling the aqueous humor. Once the pressure is regulated, stem 220 returns to its initial position tightly closing valve 200 and thus avoiding entrance of foreign objects such as dust, microorganisms, etc. to the eye.

Figure 6:
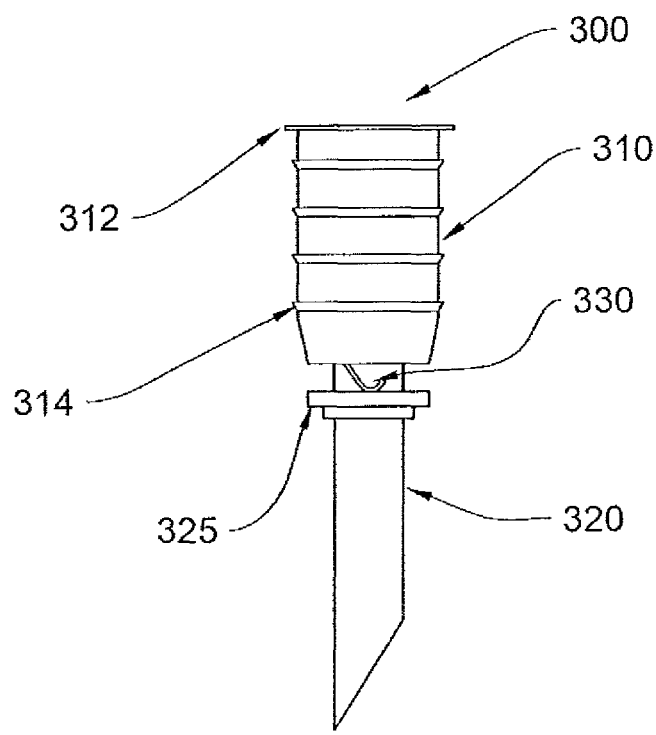
FIG. 6 is a side elevational view of a valve of the disclosure in a third embodiment.
Figure 7:
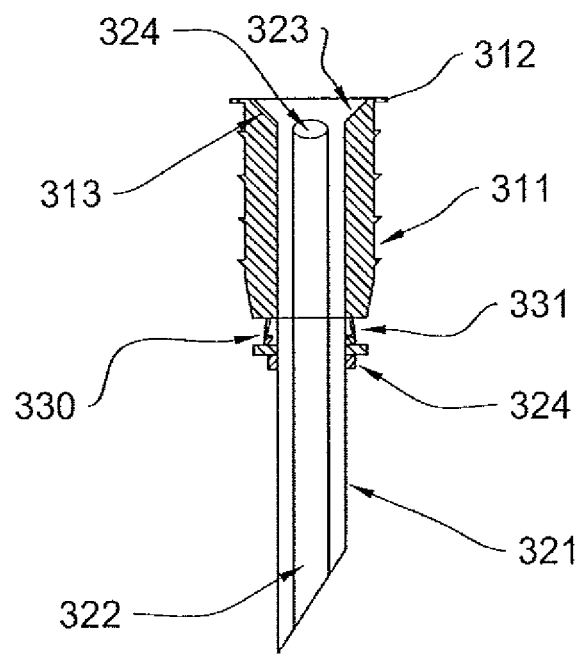
FIG. 7 is a longitudinal sectional view of the third embodiment of the valve of FIG. 6.

A third embodiment of the intraocular pressure compensating and regulating valve 300 is illustrated in FIGS. 6 and 7, and comprises a valve body 310, a stem 320 and elastic laminates or springs 330 and 331. The valve body 310 has a hollow tubular body 311 and a flange 312 in a tubular body 311 end. The stem 320 comprises a tubular body 321 with an internal canal 322 having in one of its ends, a conical part 323 resting on a seat 313, which is also conical in the part where the flange 312 is found in the valve body 310. The tubular body 321 of the stem 320, beneath the conical part 323, has radial perforations 324 in communication with the internal canal 322 of the tubular body 321 of the stem 320.

Between the valve body 310 in the end opposite flange 312 and a ring or disk 325 located on stem 320 there is a spring 330 to keep the stem 320 pressured, such that the conical part 323 is seated on seat 313 of the valve body 310. The hollow tubular body 311 includes fastening elements 314 to retain and attach the valve 300 to the cornea. Between the hollow tubular body 311 of the valve body 310 and stem 320, there is a separation from about 0.5 microns to about 3 microns, such that the stem 320 can be displaced outside the valve body 310.

Under normal conditions of intraocular pressure (about 10 to about 20 mm Hg), valve 300 remains closed and there is no aqueous humor flow outside. However, when the intraocular pressure exceeds the limit to which the spring 330 is calibrated, the stem 320 is displaced defeating the strength of spring 330, resulting in the conical part 323 of the stem 320 becoming separated from the seat 313 of the valve body 310, allowing the aqueous humor to flow through the internal canal 322 and the radial perforations 324 of the stem 320 expelling the aqueous humor. Once the pressure is regulated, stem 320 returns to its initial position tightly closing valve 300 and thus avoiding any entrance of foreign objects such as dust, microorganisms, etc. to the eye.

Figure 8:
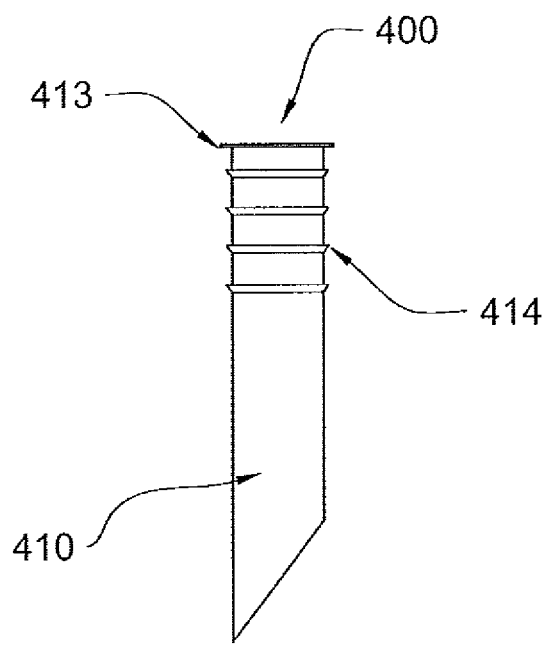
FIG. 8 is a side elevational view of a valve of the disclosure in a fourth embodiment.
Figure 9:
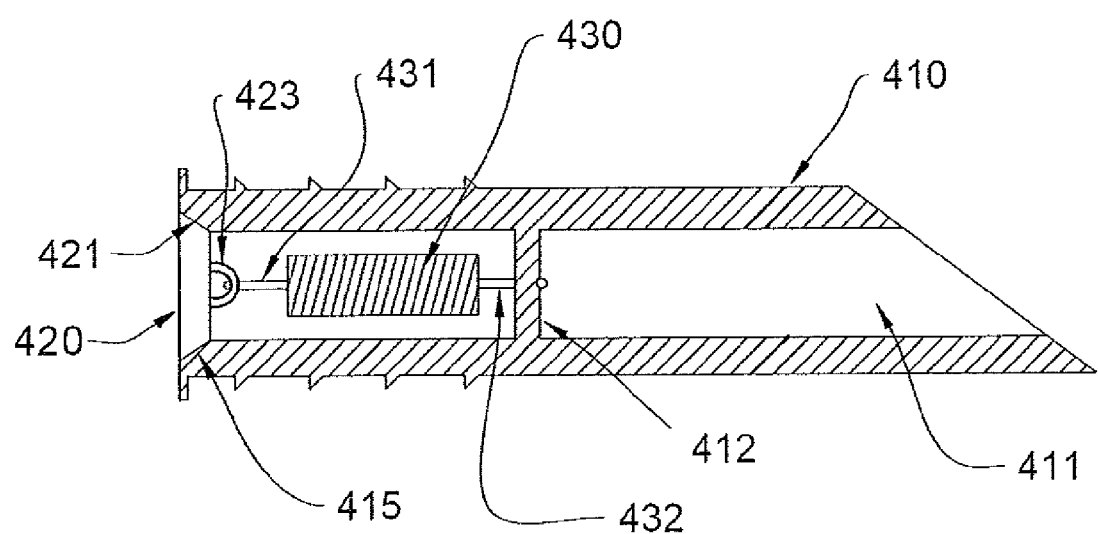
FIG. 9 is a longitudinal sectional view of the fourth embodiment of the valve of FIG. 8.

A fourth embodiment, such as is illustrated in FIGS. 8 and 9, of the intraocular pressure compensating and regulating valve 400 comprises a main body 410, a magnetic head 420, spring 430. The main body 410 is tubular body with an internal canal 411 and a spring fastening element 412 in a flange 413. The main body 410 includes a fastening element 414 to retain and attach valve 400 to the cornea.

The magnetic head 420 comprises a conical part 421 resting upon seat 415 also conical on an end of the main body 410. One rear part of the magnetic head 420 includes a hoop 423 wherein the first end 431 of the spring 430 is attached, and a second end 432 of spring 430 is attached to the fastening element 412. The spring is located inside the internal canal 411 of the main body 410.

Under normal conditions of intraocular pressure about 10 to about 20 mm Hg), valve 400 remains closed and there is no aqueous humor flow outside. However, when the intraocular pressure exceeds the limit to which the spring 430 is calibrated, the magnetic head 420 is displaced defeating the strength of spring 430 and thus forming a separation between the magnetic head 420 and seat 415 of the main body 410 allowing the aqueous humor to flow through the internal canal 411 and thus the separation formed expels the aqueous humor. Once the pressure is regulated, the magnetic head returns to its initial position tightly closing the valve and thus avoiding any entrance of foreign objects such as dust, microorganisms, etc. to the eye.

The present disclosure has been described and illustrated in multiple embodiments; however, modifications can be made, for example, geometrical modifications of the valve's parts can be made, thus comprised within the scope of the following claims.

The invention claimed is:

1. An intraocular pressure compensating and regulating valve configured to be installed inside an eye's cornea, comprising:
a valve body having a lower end and an upper end with an edge; a valve seat at the upper end; the valve seat having an upper end and being widest at its upper end, the valve seat being of a conical shape that extends to the edge of the valve body upper end; a mobile element connected to the valve seat under normal intraocular pressure conditions inside the eye, the mobile element being configured such that the mobile element separates from the valve seat when the intraocular pressure exceeds an intraocular pressure limit, the mobile element is a stem comprising a tubular body with an upper end, a lower end, an internal canal therein configured to receive aqueous humor, the stem having an upper end mobile element surface of a conical shape that rests on the conical shape of the valve seat, including at the edge of the valve body upper end, the stem having an upper part that is configured to receive aqueous humor from the internal canal and expel aqueous humor outside the valve; and an element to keep the mobile element surface in contact with the valve seat.

2. The valve in accordance with claim 1, wherein the valve body has an exterior wall with fastening elements to retain the valve to the cornea, and the element to keep the mobile element surface in contact with the valve seat is calibrated to displace the mobile element surface from the valve seat at the intraocular pressure of from about 10 to about 20 mm Hg.

3. The valve in accordance with claim 1, wherein the element for keeping the mobile element in contact with the valve seat is a spring placed on the lower part of the valve body, the stem having perforations on its upper part to expel aqueous humor outside the valve.

4. The valve in accordance with claim 2, wherein the element for keeping the mobile element in contact with the valve seat is a spring placed on the lower part of the valve body, the stem having perforations on its upper part to expel aqueous humor outside the valve.

5. The valve in accordance with claim 1, wherein the element for keeping the mobile element in contact with the valve seat is constituted by two permanent magnets with the same polarity placed on the lower part of the valve body, the stem having perforations on its upper part to expel aqueous humor outside the valve.

6. The valve in accordance with claim 2, wherein the element for keeping the mobile element in contact with the valve seat is constituted by two permanent magnets with the same polarity placed on the lower part of the valve body, the stem having perforations on its upper part to expel aqueous humor outside the valve.

7. The valve in accordance with claim 1, wherein the element for keeping the mobile element in contact with the valve seat is constituted by two springs placed in contact with one end of the valve body opposite the end where the valve seat is and a ring located in the stem, the stem having perforations on its upper part to expel aqueous humor outside the valve.

8. The valve in accordance with claim 2, wherein the element for keeping the mobile element in contact with the valve seat is constituted by two springs placed in contact with one end of the valve body opposite the end where the valve seat is and a ring located in the stem, the stem having perforations on its upper part to expel aqueous humor outside the valve.

9. The valve in accordance with claim 1, wherein the element for keeping the mobile element in contact with the valve seat is a spring having a first and second end, the spring is placed in the interior part of the valve body, and the mobile element is a magnetic head having a hoop on its lower part to hold a first end of the spring; and a second end of the spring is attached to a fastening element located on the internal part of the valve body.

10. The valve in accordance with claim 2, wherein the element for keeping the mobile element in contact with the valve seat is a spring having a first and second end, the spring is placed in the interior part of the valve body, and the mobile element is a magnetic head having a hoop on its lower part to hold a first end of the spring; and a second end of the spring is attached to a fastening element located on the internal part of the valve body.

\* \* \* \* \*